(12) United States Patent
Fenlon et al.

(10) Patent No.: US 11,235,102 B2
(45) Date of Patent: Feb. 1, 2022

(54) MEDICAMENT CONTAINER CARRIER AND ADAPTER

(71) Applicant: SANOFI-AVENTIS DEUTSCHLAND GMBH, Frankfurt am Main (DE)

(72) Inventors: Derek Fenlon, Wexford (IE); Pascal Launois, Dublin (IE); Julian McDonnell, County Wicklow (IE); Martina Moyne, County Donegal (IE); Conor Mulcahy, County Dublin (IE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 1368 days.

(21) Appl. No.: 14/775,316

(22) PCT Filed: Mar. 13, 2014

(86) PCT No.: PCT/EP2014/054922
§ 371 (c)(1),
(2) Date: Sep. 11, 2015

(87) PCT Pub. No.: WO2014/140152
PCT Pub. Date: Sep. 18, 2014

(65) Prior Publication Data
US 2016/0022907 A1 Jan. 28, 2016

(30) Foreign Application Priority Data
Mar. 14, 2013 (EP) ..................................... 13159253

(51) Int. Cl.
*A61M 5/19* (2006.01)
*A61J 1/20* (2006.01)
*A61M 5/31* (2006.01)

(52) U.S. Cl.
CPC .............. *A61M 5/19* (2013.01); *A61J 1/2096* (2013.01); *A61M 5/3129* (2013.01); *A61J 1/201* (2015.05)

(58) Field of Classification Search
CPC ....................................................... A61M 5/19
See application file for complete search history.

(56) References Cited

U.S. PATENT DOCUMENTS

| | | | |
|---|---|---|---|
| 4,664,653 | A | 5/1987 | Sagstetter et al. |
| 5,281,198 | A | 1/1994 | Haber et al. |

(Continued)

FOREIGN PATENT DOCUMENTS

| | | |
|---|---|---|
| CN | 2745588 | 12/2005 |
| CN | 1977986 | 6/2007 |

(Continued)

OTHER PUBLICATIONS

Extended European Search Report in Application No. 13159253.7, dated Sep. 19, 2013, 7 pages.

(Continued)

*Primary Examiner* — Manuel A Mendez
(74) *Attorney, Agent, or Firm* — Fish & Richardson P.C.

(57) ABSTRACT

Described is a medicament container carrier adapted to hold a first medicament container having a first predetermined size and capable of containing more than a first volume of a medicament. The container carrier comprises a body, and an adapter coupled to the body. The adapter is adapted to hold a second medicament container having a second predetermined size different from the first predetermined size and capable of containing no more than the first volume of the medicament.

19 Claims, 6 Drawing Sheets

(56) References Cited

U.S. PATENT DOCUMENTS

| | | | |
|---|---|---|---|
| 2001/0005781 A1 | 6/2001 | Bergens et al. | |
| 2005/0075602 A1 | 4/2005 | Cherif-Cheikh et al. | |
| 2006/0151049 A1 | 7/2006 | Nemoto | |
| 2011/0125100 A1 | 5/2011 | Schwirtz et al. | |
| 2011/0190693 A1 | 8/2011 | Takatsuka et al. | |
| 2012/0209192 A1* | 8/2012 | Alexandersson | A61M 5/2033 604/135 |
| 2014/0330203 A1* | 11/2014 | McLoughlin | A61M 5/172 604/131 |
| 2014/0330213 A1* | 11/2014 | Hourmand | A61M 5/24 604/187 |

FOREIGN PATENT DOCUMENTS

| | | |
|---|---|---|
| CN | 101479004 | 7/2009 |
| CN | 102014993 | 4/2011 |
| CN | 102112168 | 6/2011 |
| EP | 1124601 | 8/2001 |
| EP | 1 685 865 | 8/2006 |
| EP | 1 958 654 | 8/2008 |
| FR | 2 799 654 | 4/2001 |
| GB | 2 461 084 | 12/2009 |
| JP | 2002-528182 | 9/2002 |
| JP | 2003-511159 | 3/2003 |
| JP | 2005-523121 | 8/2005 |
| JP | 2007-511299 | 5/2007 |
| JP | 2009-518080 | 5/2009 |
| JP | 2011-156005 | 8/2011 |
| JP | 2011-524763 | 9/2011 |
| WO | WO 2003/090822 | 11/2003 |
| WO | WO 2005/002650 | 9/2007 |
| WO | WO 2008/000827 | 1/2008 |
| WO | WO 2009/153541 | 12/2009 |
| WO | WO 2014/140152 | 9/2014 |

OTHER PUBLICATIONS

International Preliminary Report on Patentability in International Application No. PCT/EP2014/054922, dated Sep. 15, 2015, 6 pages.
International Search Report and Written Opinion in International Application No. PCT/EP2014/054922, dated Apr. 1, 2014, 10 pages.
Japanese Office Action in Application No. 2015-562142, dated Dec. 5, 2017, 4 pages.

* cited by examiner

MEDICAMENT CONTAINER CARRIER AND ADAPTER

CROSS-REFERENCE TO RELATED APPLICATIONS

This application is a U.S. national stage application under 35 USC § 371 of International Application No. PCT/EP2014/054922, filed on Mar. 13, 2014, which claims priority to European Patent Application No. 13159253.7, filed on Mar. 14, 2013, the entire contents of which are incorporated herein by reference.

TECHNICAL FIELD

The invention relates to an adapter for a medicament container carrier.

BACKGROUND OF THE INVENTION

In a conventional medicament delivery device (e.g., an autoinjector), a pre-filled medicament container (e.g., syringe) is housed in a carrier which is axially movable to achieve needle penetration in an injection site and, optionally, needle withdrawal. A conventional carrier is typically sized and shaped to retain a medicament container of a predetermined size. In order to increase a dose that can be administered by the delivery device, a larger carrier would be necessary to accommodate a larger medicament container. However, a size and shape of the delivery device may not provide space for the larger medicament container. Thus, an entirely different delivery device may be necessary for different dosage amounts.

Accordingly, there is a need for a carrier and an adapter that allows the carrier to accommodate medicament containers of various sizes.

SUMMARY OF THE INVENTION

It is an object of the present invention to provide a medicament container carrier and an adapter for the medicament container carrier.

In an exemplary embodiment, a medicament container carrier adapted to hold a first medicament container having a first predetermined size and capable of containing more than a first volume of a medicament according to the present invention comprises a body, and an adapter coupled to the body. The adapter is adapted to hold a second medicament container having a second predetermined size different from the first predetermined size and capable of containing no more than the first volume of the medicament.

In an exemplary embodiment, the first volume is approximately 2 mL.

In an exemplary embodiment, the adapter includes a distal rib adapted to abut a distal end of the second medicament container.

In an exemplary embodiment, the adapter includes at least one opening providing visual access to the second medicament container.

In an exemplary embodiment, the adapter includes at least one resilient arm adapted to engage the second medicament container. The arm includes a first ramp adapted to engage a distal face of a flange to deflect the arm in a first radial direction. The arm includes a first abutment surface adapted to engage the flange to prevent rotation of the second medicament container relative to the adapter and a second abutment surface adapted to engage the flange to prevent axial displacement of the second medicament container relative to the adapter. The arm includes a second ramp adapted to engage an engagement element on the body to deflect the arm in a second radial direction. The arm includes a third abutment surface adapted to abut a proximal stop in the body to prevent axial displacement of the adapter relative to the body, and a fourth abutment surface adapted to engage a restricting surface in the body to prevent rotation of the adapter relative to the body. The proximal stop is formed in an aperture on the body.

In an exemplary embodiment, the first medicament container and the second medicament container are each one of a pre-filled syringe and a medicament cartridge.

In an exemplary embodiment, a medicament delivery device according to the present invention comprises a housing, and a medicament container carrier according to the exemplary embodiments described herein. The medicament container carrier may be slidably disposed in the housing.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
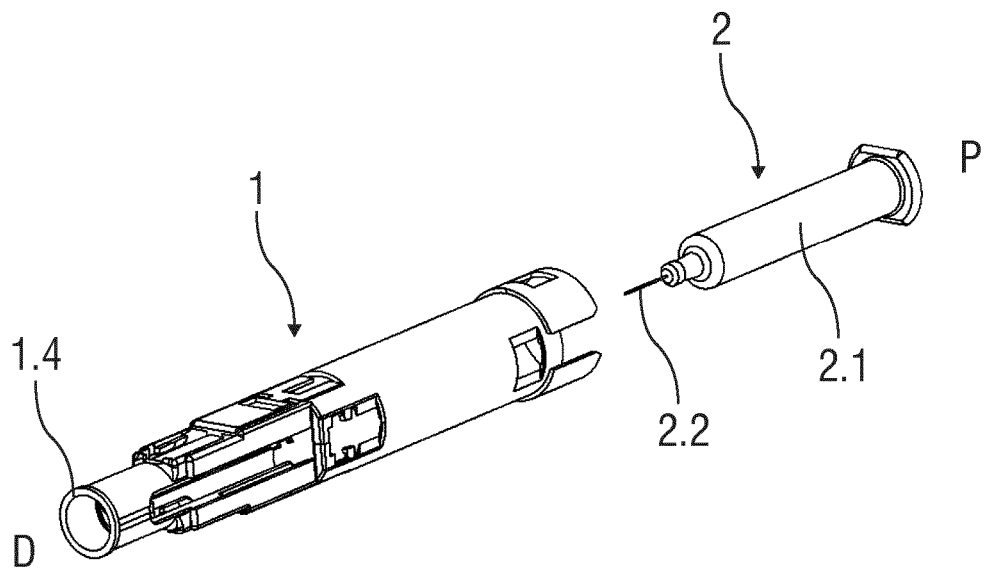
FIG. 1 is a schematic perspective exploded view of an exemplary embodiment of a container carrier and a first medicament container according to the present invention.

FIG. 1 is a schematic perspective exploded view of an exemplary embodiment of a container carrier 1 having a body adapted to hold a first medicament container 2 according to the present invention. The first medicament container 2, which may be a syringe, an ampoule, a cartridge, etc., has a first predetermined size (e.g., length, diameter, etc.) and contains up to a first maximum amount of a medicament. For example, the first medicament container 2 may be a pre-filled syringe containing a 2 mL dose of a medicament.

In an exemplary embodiment, the first medicament container 2 comprises a medicament container body 2.1, a needle 2.2 mounted to a distal end of the medicament container body 2.1 and in fluid communication with a cavity defined within the medicament container body 2.1 for containing a medicament, and a stopper (not illustrated) disposed within the cavity near a proximal end of the medicament container body 2.1, wherein the stopper proximally seals the cavity and can be axially displaced within the cavity for expelling the medicament through the needle 2.2. The needle 2.2 may fixed to the container body 2.1 or may be removably coupled thereto. In the latter exemplary embodiment, the needle 2.2 may be a double-tipped needle and the distal end of the body 2.1 may include a septum which receives a proximal tip of the needle 2.2.

Figure 2:
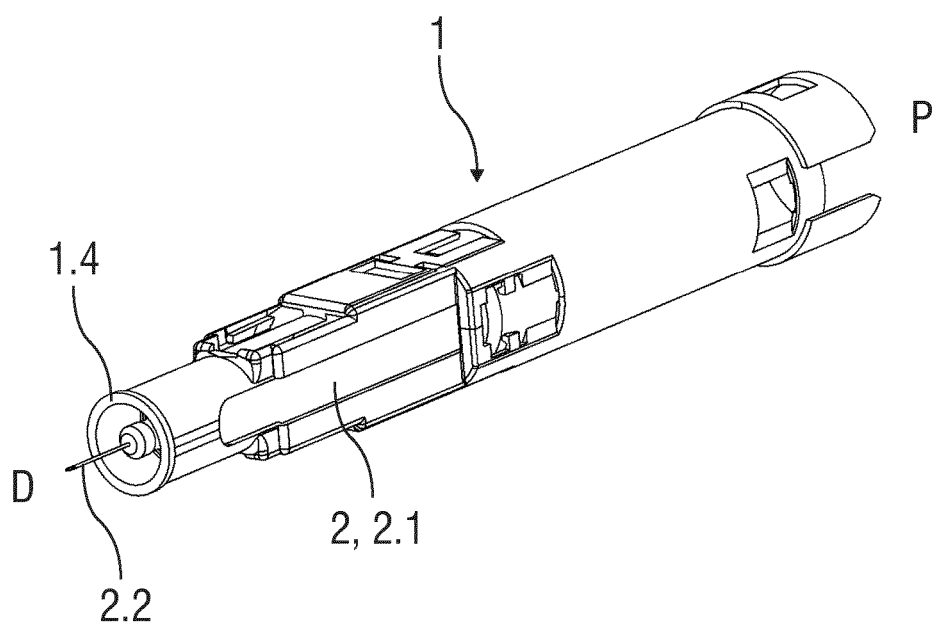
FIG. 2 is a schematic perspective view of an exemplary embodiment of a container carrier coupled to a first medicament container according to the present invention.

FIG. 2 is a schematic perspective view of an exemplary embodiment of the container carrier 1 with the first medicament container 2 coupled thereto. The first medicament container 2 may be inserted into a proximal opening of the container carrier 1 and moved distally until it abuts a distal stop. A retention mechanism (e.g., snaps, clips, locks, etc.) in the container carrier 1 may engage a proximal end (e.g., flange(s)) of the first medicament container 2 to prevent the first medicament container 2 from translating axially relative to the container carrier 1 and/or rotating relative to the container carrier 1.

Figure 3:
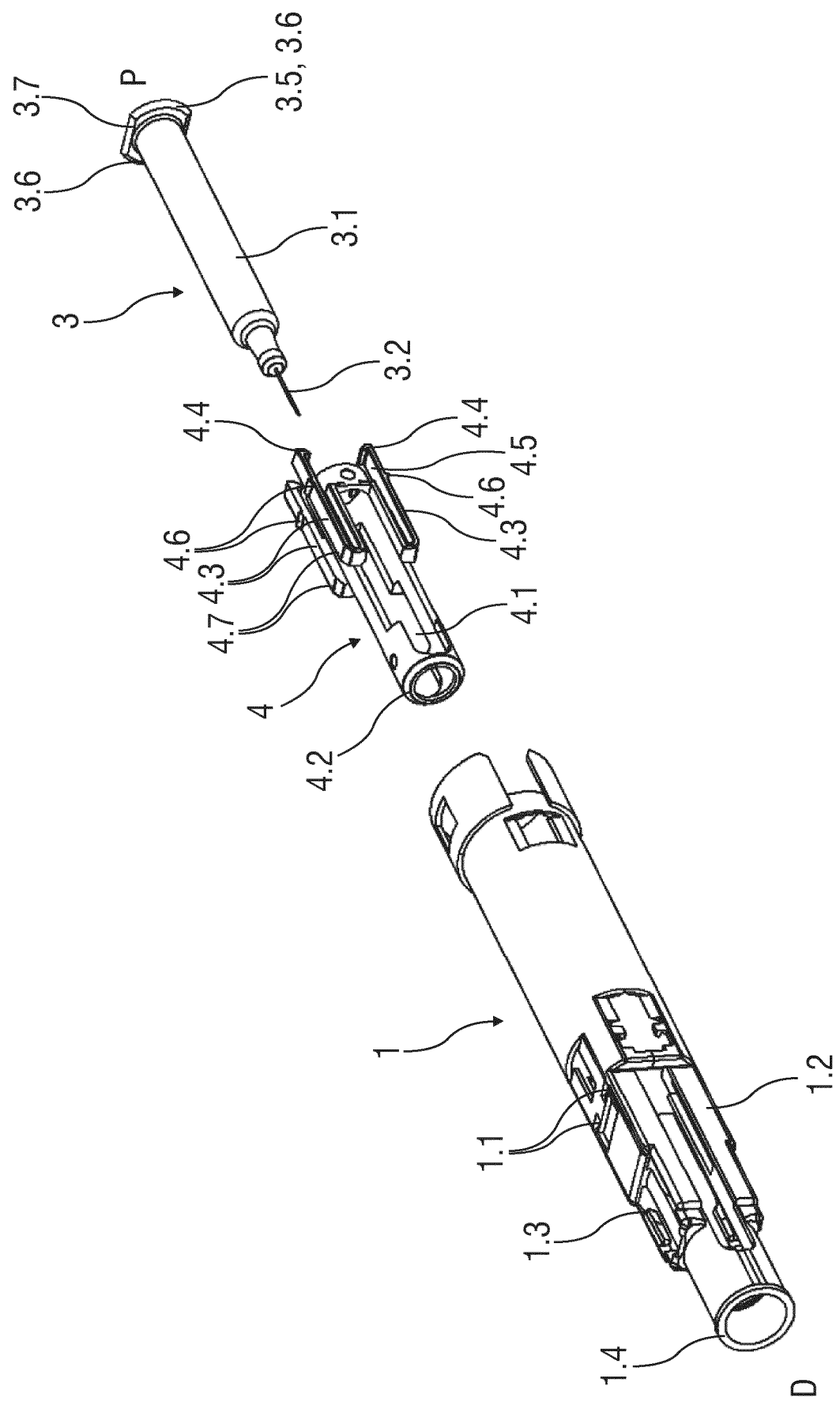
FIG. 3 is a schematic perspective exploded view of an exemplary embodiment of a container carrier, an adapter and a second medicament container according to the present invention.
Figure 4:
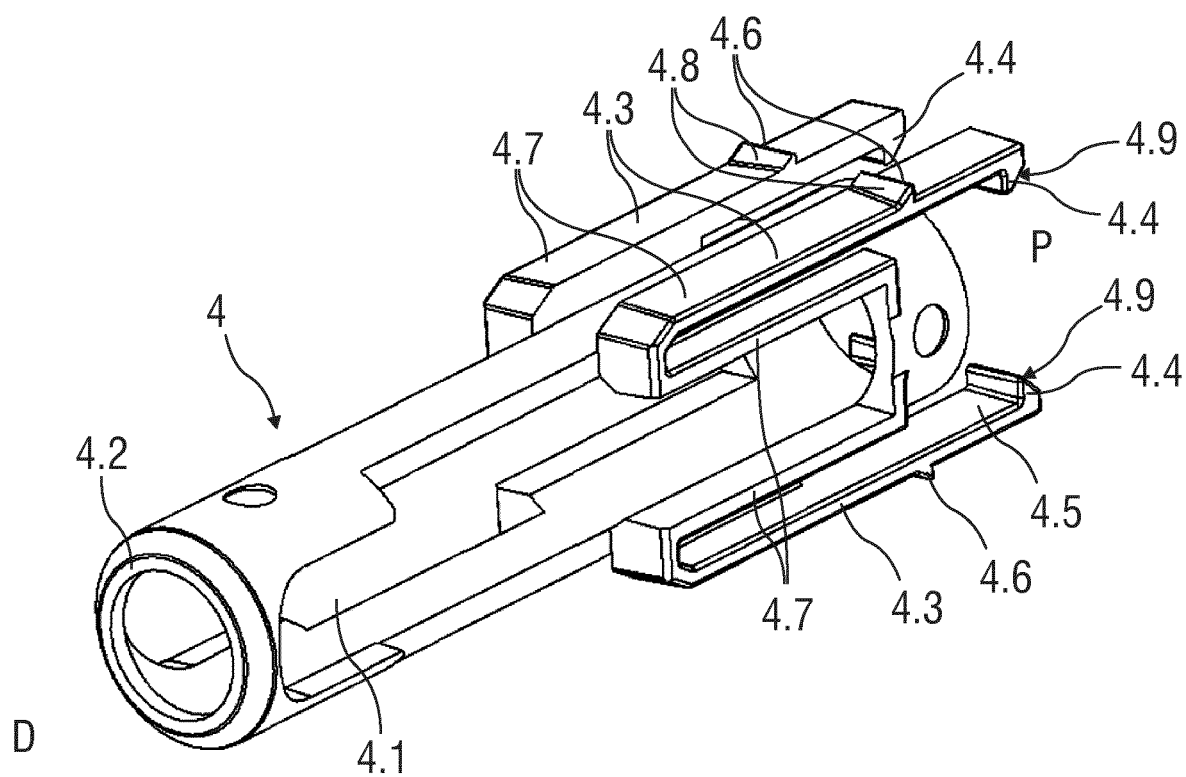
FIG. 4 is a schematic perspective view of an exemplary embodiment of an adapter according to the present invention.

FIG. 3 is a schematic perspective exploded view of an exemplary embodiment of the container carrier 1, an adapter 4 and a second medicament container 3. FIG. 4 is a schematic perspective view of an exemplary embodiment of the adapter 4.

In an exemplary embodiment, the adapter 4 is designed to engage a second medicament container 3 having a second predetermined size smaller than the first predetermined size of the first medicament container 2. The adapter 4 may further be designed to engage the container carrier 1. The second medicament container 3 comprises a medicament container body 3.1, a needle 3.2 mounted to a distal end of the medicament container body 3.1 and in fluid communication with a cavity defined within the medicament container body 3.1 for containing a medicament, and a stopper (not illustrated) disposed within the cavity near a proximal end of the medicament container body 3.1, wherein the stopper proximally seals the cavity and can be axially displaced within the cavity for expelling the medicament through the needle 3.2. The needle 3.2 may fixed to the container body 3.1 or may be removably coupled thereto. In the latter exemplary embodiment, the needle 3.2 may be a double-tipped needle and the distal end of the body 3.1 may include a septum which receives a proximal tip of the needle 3.2. A flange 3.5 may be arranged at a proximal end of medicament container body 3.1. In an exemplary embodiment, the flange 3.5 comprises two arc sections 3.6 connected by two straight sections 3.7.

In an exemplary embodiment, the adapter 4 may be used to allow a medicament delivery device (e.g., a pen injector, an auto-injector, etc.) to accommodate various medicament container sizes. The adapter 4 may allow the usage of a common delivery device for different medicament container sizes. Therefore, a reduction in device costs and consistency in medicament administration may be achieved.

In an exemplary embodiment, the adapter 4 is adapted to retain the second medicament container 3 such that the second medicament container 3 is axially and rotationally fixed within the adapter 4. The adapter 4 is also adapted to be retained within the container carrier 1 such that the adapter 4 is axially and rotationally fixed within the container carrier 1. Preventing rotation of the second medicament container 3 prevents the needle 3.2 from rotating during an injection thus reducing the risk for bending and distorting the needle 3.2 which may otherwise result in pain. Preventing axial movement of the medicament container 3 in a proximal direction P also prevents the second medicament container 3 from being pushed in the proximal direction P relative to the adapter 4 and the container carrier 1 upon contact of the needle 3.2 with an injection site.

In an exemplary embodiment as shown in FIG. 4, the adapter 4 may be sized and/or shaped to telescopically engage the container carrier 1 and the second medicament container 3. For example, the adapter 4 may have an outer geometry which corresponds to an inner shape of the container carrier 1 and an inner geometry which corresponds to the second predetermined size/shape of the second medicament container 3. A distal rib 4.2 formed on a distal end of the adapter 4 may be adapted to abut the distal end of the container body 3.1 to prevent distal movement of the second medicament container 3 beyond the distal rib 4.2.

In an exemplary embodiment, the adapter 4 may include one or more lateral openings 4.1 for allowing inspection of the contents and state of the second medicament container 3. In another exemplary embodiment, the adapter 4 may be made from a transparent/translucent material to provide visual access to the contents of the second medicament container 3.

Figure 5:
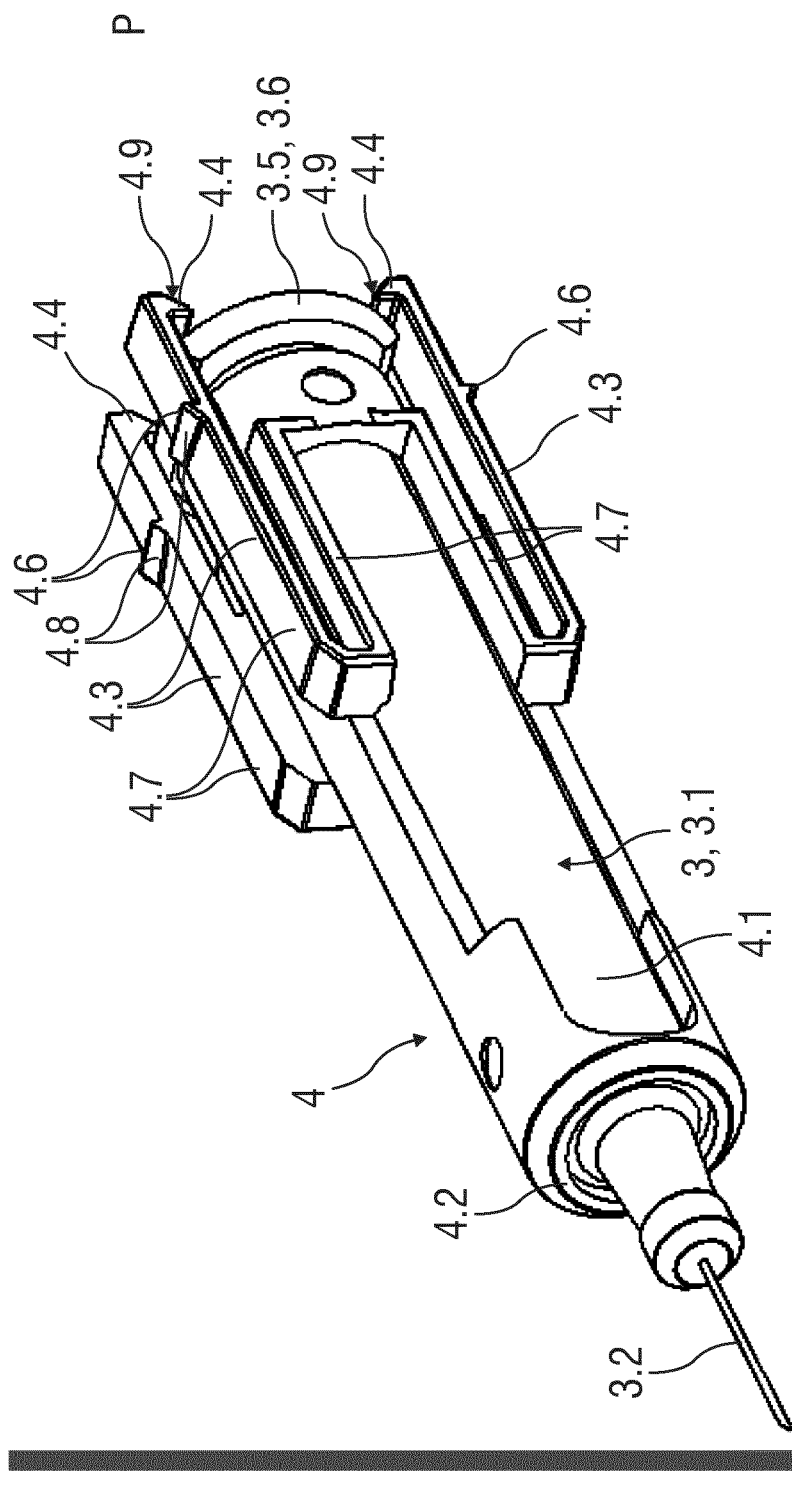
FIG. 5 is a schematic perspective view of an exemplary embodiment of a second medicament container coupled to an adapter according to the present invention.

In an exemplary embodiment, the adapter 4 may comprise at least one resilient arm 4.3 extending proximally and adapted to engage a proximal portion (e.g., the flange 3.5) of the container body 3.1. In the exemplary embodiment shown in FIG. 4, the adapter 4 includes four resilient arms 4.3. The arm 4.3 may include features to facilitate insertion and retention of the second medicament container 3. For example, a proximal end of the arm 4.3 may include a first ramp 4.9 which is adapted to engage the flange 3.5 (e.g., the straight section 3.7) when the second medicament container 3 is inserted into the adapter 4. As the flange 3.5 engages the first ramp 4.9, the arm 4.3 is deflected in a first radial direction until the flange 3.5 bypasses the ramped face 4.9. As shown in FIG. 5, when the arm 4.3 returns to a non-deflected position, a first abutment surface 4.5 may engage the flange 3.5 (e.g., straight section 3.7) and thereby prevent the second medicament container 3 from rotating relative to the adapter 4, and a second abutment surface 4.4 may abut a proximal face of the flange 3.5 and thereby prevent the second medicament container 3 from moving axially relative to the adapter 4.

Referring back to the exemplary embodiment shown in FIG. 4, the resilient arm 4.3 may include a second ramp 4.8, a third abutment surface 4.6, and a fourth abutment surface 4.7 which facilitate insertion and retention of the adapter 4 by the container carrier 1. For example, the second ramp 4.8 may be disposed on a radially outer surface of the arm 4.3. When the adapter 4 is inserted into the container carrier 1, the second ramp 4.8 may engage an element or an aperture 1.1 on the container carrier 1, which causes the arm 4.3 to deflect in a second radial direction (opposite the first radial direction) until the second ramp 4.8 bypasses the element. When the arm 4.3 returns to the non-deflected position, the third abutment surface 4.6 may engage a proximal stop in the container carrier 1 and thereby prevent axial displacement of the adapter 4 relative to the container carrier 1. The fourth abutment surface 4.7 may engage a surface or element in the container carrier 1 to prevent rotation of the adapter 4 relative to the container carrier 1.

Figure 6:
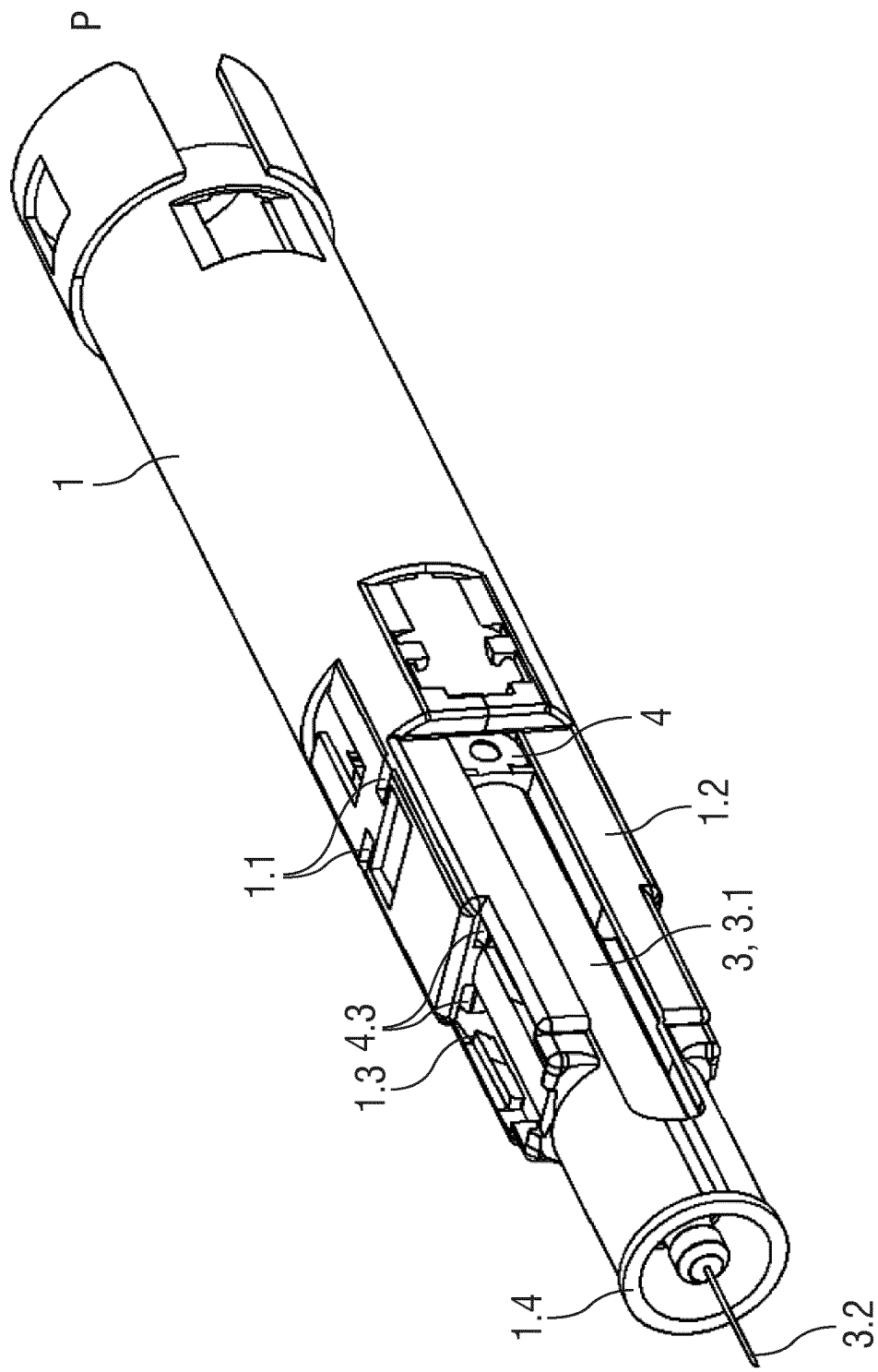
FIG. 6 is a schematic perspective view of an exemplary embodiment of a container carrier coupled to an adapter and a second medicament container according to the present invention.
Figure 7:
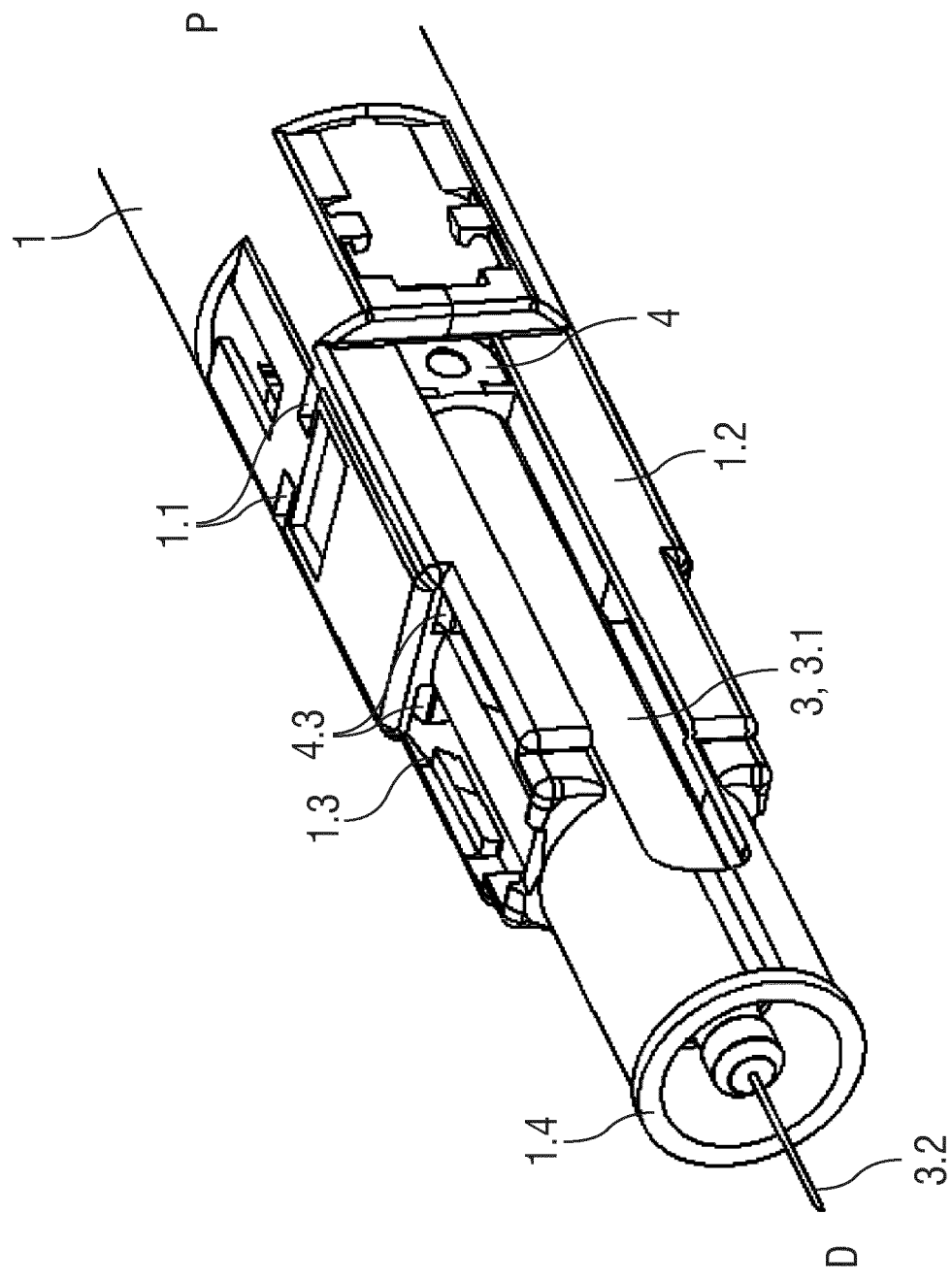
FIG. 7 is a schematic perspective detail view of an exemplary embodiment of a container carrier coupled to an adapter and a second medicament container according to the present invention.

The second medicament container 3 may be assembled with the container carrier 1 as shown in FIGS. 6 and 7 in at least two ways. In a first exemplary process, the adapter 4 may be inserted into the container carrier 1 and translated distally until it abuts a distal stop 1.3 and the third abutment surface 4.6 abuts proximal stop. The second medicament container 3 may then be inserted into the adapter 4 and translated distally until it abuts the distal rib 4.2 and the second abutment surface 4.4 abuts the flange 3.5. In a second exemplary process, the second medicament container 3 may be inserted into the adapter 4, and the adapter 4 may then be inserted into the container carrier 1.

In an exemplary embodiment, the first medicament container 2 may be adapted to contain greater than approximately 2 mL of a medicament, and the second medicament container may be adapted to contain less than approximately 2 mL of a medicament.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A medicament container carrier comprising:
    a body configured to securely engage a first medicament container to hold the first medicament container directly within the body, the body being configured for removal of the first medicament container from the body, the first medicament container having a first predetermined size and having a first volume capacity that is greater than a first volume of a medicament; and
    an adapter adapted to hold a second medicament container having a second predetermined size that is different from the first predetermined size and having a second volume capacity that is no more than the first volume of the medicament,
    wherein the adapter is separate from the body and configured to be inserted directly into the body to axially and rotationally fix the adapter to the body when the body is free of the first medicament container.

2. The medicament container carrier of claim 1, wherein the first volume capacity is approximately 2 mL.

3. The medicament container carrier of claim 1, wherein the adapter comprises a distal rib adapted to abut a distal end of the second medicament container.

4. The medicament container carrier of claim 1, wherein the adapter comprises at least one opening providing visual access to the second medicament container.

5. The medicament container carrier of claim 1, wherein the adapter comprises at least one resilient arm adapted to engage the second medicament container.

6. The medicament container carrier of claim 5, wherein the at least one resilient arm comprises a first ramp adapted to engage a distal face of a flange of the second medicament container to deflect the at least one resilient arm in a first radial direction.

7. The medicament container carrier of claim 6, wherein the at least one resilient arm further comprises:
    a first abutment surface adapted to engage the flange to prevent rotation of the second medicament container about a longitudinal axis of the adapter relative to the adapter, and
    a second abutment surface adapted to engage the flange to prevent axial displacement of the second medicament container relative to the adapter.

8. The medicament container carrier of claim 7, wherein the at least one resilient arm further comprises:
    a second ramp adapted to engage an engagement element on the body to deflect the at least one resilient arm in a second radial direction.

9. The medicament container carrier of claim 8, wherein the at least one resilient arm further comprises:
    a third abutment surface adapted to abut a proximal stop in the body to prevent axial displacement of the adapter relative to the body, and
    a fourth abutment surface adapted to engage a restricting surface in the body to prevent rotation of the adapter about a longitudinal axis of the body relative to the body.

10. The medicament container carrier of claim 9, wherein the proximal stop is formed in an aperture on the body.

11. The medicament container carrier of claim 1, wherein the first medicament container and the second medicament container are each one of a pre-filled syringe and a medicament cartridge.

12. A medicament delivery device comprising:
    a housing; and
    a medicament container carrier slidably disposed in the housing the medicament container carrier comprising:
        a body configured to securely engage a first medicament container to hold the first medicament container directly within the body, the body being configured for removal of the first medicament container from the body, the first medicament container having a first predetermined size and having a first volume capacity that is greater than a first volume of a medicament, and
        an adapter adapted to hold a second medicament container having a second predetermined size that is different from the first predetermined size and having a second volume capacity that is no more than the first volume of the medicament,
        wherein the adapter is separate from the body and configured to be inserted directly into the body to axially and rotationally fix the adapter to the body when the body is free of the first medicament container.

13. The medicament delivery device of claim 12, wherein the first volume capacity is approximately 2 mL.

14. The medicament delivery device of claim 12, wherein the adapter comprises a distal rib adapted to abut a distal end of the second medicament container.

15. The medicament delivery device of claim 12, wherein the adapter comprises at least one opening providing visual access to the second medicament container.

16. The medicament delivery device of claim 12, wherein the adapter comprises at least one resilient arm adapted to engage the second medicament container.

17. The medicament delivery device of claim 16, wherein the at least one resilient arm comprises:
    a first ramp adapted to engage a distal face of a flange to deflect the at least one resilient arm in a first radial direction, a first abutment surface adapted to engage the flange to prevent rotation of the second medicament container relative to the adapter, a second abutment surface adapted to engage the flange to prevent axial displacement of the second medicament container relative to the adapter, a second ramp adapted to engage an engagement element on the body to deflect the at least one resilient arm in a second radial direction, a third abutment surface adapted to abut a proximal stop in the body to prevent axial displacement of the adapter relative to the body, the proximal stop being formed in an aperture on the body, and a fourth abutment surface adapted to engage a restricting surface in the body to prevent rotation of the adapter relative to the body.

18. The medicament delivery device of claim 12, wherein the first medicament container and the second medicament container are each one of a pre-filled syringe and a medicament cartridge, and wherein the medicament delivery device is an auto-injector.

19. A medicament container carrier comprising:

a body configured to securely engage a first medicament container to hold the first medicament container directly within the body, the body being configured for removal of the first medicament container from the body, the first medicament container having a first predetermined size and having a first volume capacity that is greater than a first volume of a medicament; and an adapter adapted to hold a second medicament container having a second predetermined size that is different from the first predetermined size and having a second volume capacity that is no more than the first volume of the medicament, wherein the adapter is separate from the body and configured to be inserted directly into the body to couple the adapter to the body when the body is free of the first medicament container, wherein the adapter comprises at least one resilient arm adapted to engage the second medicament container, wherein the at least one resilient arm comprises a U-shaped portion, and wherein the at least one resilient arm is adapted to engage the body.

* * * * *